US010117435B2

(12) United States Patent
Willette et al.

(10) Patent No.: US 10,117,435 B2
(45) Date of Patent: Nov. 6, 2018

(54) COMPOSITION CONTAINING AN ORGANOSILANE AND A PHOTOCATALYST, AND METHODS OF TREATING FLOWERING PLANTS INFECTED WITH A BACTERIAL DISEASE USING THE COMPOSITION

(71) Applicant: Nano Photo Sciences, LLC, Tequesta, FL (US)

(72) Inventors: Christopher C. Willette, Tequesta, FL (US); Thomas D. Anspach, Jupiter, FL (US)

(73) Assignee: Nano Photo Sciences, LLC, Tequesta, FL (US)

( * ) Notice: Subject to any disclaimer, the term of this patent is extended or adjusted under 35 U.S.C. 154(b) by 0 days.

(21) Appl. No.: 15/055,198

(22) Filed: Feb. 26, 2016

(65) Prior Publication Data

US 2016/0249621 A1 Sep. 1, 2016

Related U.S. Application Data

(60) Provisional application No. 62/126,180, filed on Feb. 27, 2015.

(51) Int. Cl.
*A01N 55/00* (2006.01)
*B01J 21/06* (2006.01)
*B01J 35/00* (2006.01)
*A01N 59/16* (2006.01)

(52) U.S. Cl.
CPC ............ *A01N 55/00* (2013.01); *A01N 59/16* (2013.01); *B01J 21/063* (2013.01); *B01J 35/004* (2013.01); *B01J 35/0013* (2013.01)

(58) Field of Classification Search
CPC ..... A01N 55/00; B01J 35/004; B01J 35/0013; B01J 35/063
USPC .......................................................... 514/63
See application file for complete search history.

(56) References Cited

U.S. PATENT DOCUMENTS

| 5,064,613 A | 11/1991 | Higgs et al. |
| 6,572,926 B1 | 6/2003 | Morgan et al. |
| 6,613,755 B2 | 9/2003 | Peterson et al. |
| 8,372,443 B2 | 2/2013 | Rouseff et al. |
| 8,609,121 B2 | 12/2013 | Averett et al. |
| 8,632,811 B1 | 1/2014 | Santra |
| 8,795,736 B2 | 8/2014 | Huber |
| 2009/0074971 A1* | 3/2009 | McMahon ............. A01N 55/00 427/314 |
| 2013/0259954 A1 | 10/2013 | Masaoka et al. |

FOREIGN PATENT DOCUMENTS

| EP | 1146099 | 10/2001 |
| JP | 2004105087 | 4/2004 |
| JP | 2006312730 | 11/2006 |
| JP | 2007275731 | 10/2007 |
| KR | 20130013887 | 2/2013 |
| WO | WO2010027783 | 3/2010 |
| WO | WO2012151407 | 11/2012 |
| WO | WO2013077805 | 5/2013 |

OTHER PUBLICATIONS

Messaoud et al., J. Mater. Sci. Technol., (2014), 30(1), p. 19-29.*
The Gardener's Pantry, Citrus scale, posted Mar. 15, 2007.*
Buzby et al. J. of Vacuum Science & Technology B:Microelectronics and Nanometer Structures Processing, Measurnement, and Phenomena, (2006) 24, 1210-1214.*
Natural Pesticides, Brooklyn Botanic Garden (1994), p. 1-14.*

* cited by examiner

*Primary Examiner* — Yong L Chu
(74) *Attorney, Agent, or Firm* — McHale & Slavin, P.A.

(57) ABSTRACT

The present invention relates to a composition for treating plants inflicted with a bacterial disease transmitted by a psyllid vector, and methods of treating plant disease transmitted by a psyllid vector. The composition comprises an organosilane, preferably an organosilane quaternary ammonium, and a photocatalyst, such as titanium dioxide.

12 Claims, 15 Drawing Sheets

COMPOSITION CONTAINING AN ORGANOSILANE AND A PHOTOCATALYST, AND METHODS OF TREATING FLOWERING PLANTS INFECTED WITH A BACTERIAL DISEASE USING THE COMPOSITION

In accordance with 37 C.F.R. 1.76, a claim of priority is included in an Application Data Sheet filed concurrently herewith. Accordingly, the present invention claims priority to U.S. Provisional Patent Application No. 62/126,180, entitled "COMPOSITION CONTAINING AN ORGANOSILANE AND A PHOTOCATALYST, AND METHODS OF TREATING FLOWERING PLANTS INFECTED WITH A BACTERIAL DISEASE USING THE COMPOSITION", filed Feb. 27, 2015. The contents of the above referenced application are incorporated herein by reference in their entirety.

FIELD OF THE INVENTION

The present invention relates to a composition for preventing plant disease; to a composition and method of using the composition for preventing plant disease associated with plants and crops containing organosilane and a photocatalyst, and more importantly to a composition and method of using the composition for preventing disease in flowering plants containing organosilane quaternary ammonium in combination with a light activated photocatalytic element.

BACKGROUND OF THE INVENTION

Agriculture is a multibillion dollar, international industry. One area of importance is the production of fruits by cultivating flowering plants. Citrus, characterized by plants that produce fragrant flowers and edible juicy fruits such as oranges, grapefruits, lemons, and tangerines, is a common term and genus of flowering plants in the rue family. Cultivating and the production of commercial citrus products play an important role in the economies of many countries. For example, Florida's citrus industry is a multibillion dollar industry employing tens of thousands of jobs. While Florida's orange industry has weathered hardships associated with canker disease, hurricanes, and hard freezes, the industry has faced its toughest challenge recently with the introduction of a bacterial disease known as citrus greening.

Huanglongbing (HLB), or citrus greening disease, is a plant based disease spread by the Asian citrus psyllid, *Diaphorina citri Kuwayama* and *Trioza erytreae*. It was first reported in China in the early 1900s, but has spread to many citrus producing regions. HLB is caused by a phloem-limited bacterial pathogen, *Candidatus Liberibacter*. The bacterial pathogen plugs the phloem (plant's vasculature tissue), thereby limiting nutrient movement. Once infected, the citrus plant eventually produces inedible fruits. Early symptoms of the disease include yellowing of the leaves on an individual limb or in sections of the tree. The leaves that turn yellow have asymmetrical patterns of blotchy yellowing, or molting of the leaf. As the disease progresses, the fruit size becomes smaller and the juice turns bitter. Eventually, the fruit becomes lopsided, has dark aborted seeds, and tends to drop prematurely. There is presently no known cure for plants infected with HLB. Applying foliage nutrients provides temporary delay of various symptoms of the infection. However, the bacteria remain alive and active, resulting in the decline in usable fruit production. Introduction of antibiotics into the tree's vasculature systems via injections is not viable as such substances tend to be toxic. Moreover, surface applied copper compounds are not sufficient to inhibit bacterial activity within the xylem and phloem of the plant. As such, current HLB strategies include insecticide sprays to limit the populations of the psyllid or the removal of infected plants and repopulation. Such methods, however, are time consuming, costly, and fail to prevent new plants from becoming infected.

Accordingly, there is a need in the art for an effective composition, and method of using the composition, to treat diseases associated with flowering plants, such as citrus plants.

DESCRIPTION OF THE PRIOR ART

Various compositions have been proposed to treat citrus greening disease. For example, U.S. Pat. No. 8,795,736 describes a composition using copper phosphite and nutrient halo-phosphite compounds. U.S. Pat. No. 8,372,443 describes a method which utilizes volatile compounds of hydrogen sulfide, methanethiol, sulfur dioxide, dimethyl sulfide, dimethyl disulfide, methional, or dimethyl trisulfide to treat the citrus greening disease. U.S. Patent Application Publication No. 2013/0259954 describes a liquid treatment containing Fe ions, where some of the Fe ions are $Fe^{2+}$ ions.

SUMMARY OF THE INVENTION

The present invention describes an environmentally friendly microbiocide for use in treating plant based disease. The composition is formulated utilizing light activated chemistry for the purpose of disinfecting bacteria, mold, and plant based pathogens, such as Huanglongbing (HLB), or citrus greening disease. The composition comprises an organosilane and a photocatalyst. In one embodiment of the invention, the composition comprises an organosilane quaternary ammonium in combination with a light activated photocatalytic element. In another embodiment, the composition comprises an organosilane quaternary ammonium in combination with titanium dioxide. In any embodiment, the organosilane and the photocatalyst are provided in effective amounts to treat diseased flowering plants, such as citrus plants infected with HLB.

The composition has several characteristics that are believed to be responsible for its effectiveness in treating plants inflicted with bacterial diseases. It is theorized the composition provides protection from bacterial disease based on several processes. First, plant surface and inter-vascular protection is based on a process utilizing broad spectrum sunlight which activates (nano) particle metal-oxide crystalline mineral catalyst. This process is generally known as photocatalytic oxidation. The catalyst reacts with energy from light photons to create a surface borne reactive oxidant that can neutralize bacteria, viral and fungal strains. This protects the plant from environmental pathogens such as fungi and invading bacteria. Second, the composition provides a surface and intervascular organosilane salt crystalline surfactant anti-microbial process. This process is effective at both impaling surface born microbes on the outside of the plant, as well as through absorption via stoma sites or roots and circulation within the plant to act as an osmo-protectorant. On the surface of the plant, the composition has the affinity to attract pathogens and impale them via a rigid organosilane salt crystal bound to the plant's surface. This protects the plant from invading pathogens such as fungi and bacteria. The same salt surfactant chemistry has a symbiotic affect as an osmo-protectorant within the plant. This assists the plant by providing drought resistance, as well as assisting in the photosynthesis process. Finally, the composition may act as an (nano molecule) oxidizer. In this case, nano particle molecules are specifically engineered for absorption into the plant's xylem system via stomata sites or via root drenching to attack specific plant pathogenic protein genes. This process reduces the pathogens through reactive oxidative stress (ROS) and a potential gene pairing and stunting process which prevents replication and reduces and eliminates the invading pathogens.

As used herein, the term "effective amount" generally refers to an amount of the composition; for example, the amount of a compound as an active ingredient that is sufficient to effect treatment as defined herein when administered to a plant, such as a flowering plant, preferably a citrus plant in need of such treatment. An effective amount of the composition compound of the present invention will depend on a number of factors including, for example, the type of plant, the precise condition requiring treatment and its severity, and the route of administration.

As used herein, the term "treat", "treating" or "treatment" refers to the administration or application of the composition to a plant, particularly a flowering plant, more particularly a citrus plant, which already manifests at least one symptom of a disease such as, but not limited to, Huanglongbing (HLB), or citrus greening disease, to obtain a desired pharmacological and physiological effect. The term may also include preventing the disease, i.e., causing the clinical symptoms of the disease not to develop in a plant that may be exposed to or predisposed to the disease but does not yet experience or display symptoms of the disease, inhibiting the disease, i.e. arresting or reducing the development of the disease or its clinical symptoms, or relieving the disease, i.e., causing regression of the disease or its clinical symptoms.

As used herein, the term "photocatalyst" refers to a reaction which uses light to activate a substance which modifies the rate of a chemical reaction without being involved itself; the photocatalyst is the substance which can modify the rate of the chemical reaction using light irradiation.

Accordingly, it is an objective of the present invention to provide a composition to treat plants having a bacterial disease.

It is a further objective of the present invention to provide a method of treating plants suffering from a bacterial disease.

It is yet another objective of the present invention to provide a composition, and method of using the composition, to treat plants suffering from a disease transmitted by psyllids.

It is a still further objective of the invention to provide a composition, and method of using the composition, to treat plants suffering from a disease transmitted by *Diaphorina citri Kuwayama* or *Trioza erytreae*.

It is a further objective of the present invention to provide a composition, and method of using the composition, to treat plants infected with phloem-limited bacterial pathogens.

It is yet another objective of the present invention to provide a composition, and method of using the composition, to treat plants infected with *Candidatus Liberibacter*.

It is a still further objective of the invention to provide a composition, and method of using the composition, to treat flowering plants suffering from a disease transmitted by psyllids.

It is a further objective of the present invention to provide a composition, and method of using the composition, to treat flowering plants suffering from a disease transmitted by plants suffering from a disease transmitted by *Diaphorina citri Kuwayama* or *Trioza erytreae*.

It is yet another objective of the present invention to provide a composition, and method of using the composition, to treat flowering plants infected with phloem-limited bacterial pathogens.

It is a further objective of the present invention to provide a composition, and method of using the composition, to treat flowering plants infected with *Candidatus Liberibacter*.

It is yet another objective of the present invention to provide a composition to treat flowering plants suffering from Huanglongbing (HLB), or citrus greening disease.

It is a still further objective of the invention to provide a method of treating flowering plants suffering from Huanglongbing (HLB), or citrus greening disease.

It is yet another objective of the present invention to provide a composition to treat citrus plants suffering from Huanglongbing (HLB), or citrus greening disease.

It is a still further objective of the invention to provide a method of treating citrus plants suffering from Huanglongbing (HLB), or citrus greening disease.

It is yet another objective of the present invention to provide a composition comprising an organosilane quaternary ammonium in combination with a light activated photocatalytic element to treat flowering plants suffering from Huanglongbing (HLB), or citrus greening disease.

It is a still further objective of the invention to provide a method of treating flowering plants suffering from Huanglongbing (HLB), or citrus greening disease, comprising application of a composition of organosilane quaternary ammonium in combination with a light activated photocatalytic element.

It is yet another objective of the present invention to provide a composition comprising an organosilane quaternary ammonium in combination with a light activated photocatalytic element to treat citrus plants suffering from Huanglongbing (HLB), or citrus greening disease.

It is a still further objective of the invention to provide a method of treating citrus plants suffering from Huanglongbing (HLB), or citrus greening disease, comprising application of a foliar spray of a composition of organosilane quaternary ammonium in combination with a light activated photocatalytic element to citrus plants infected with Huanglongbing (HLB).

It is yet another objective of the invention to provide a method of treating citrus plants suffering from Huanglongbing (HLB), or citrus greening disease, comprising application of a root drench of a composition of organosilane quaternary ammonium in combination with a light activated photocatalytic element to citrus plants infected with Huanglongbing (HLB).

It is a further objective of the invention to provide a method of treating citrus plants suffering from Huanglongbing (HLB), or citrus greening disease, comprising application of foliar spray and a root drench of a composition of organosilane quaternary ammonium in combination with a light activated photocatalytic element to citrus plants infected with Huanglongbing (HLB).

Other objectives and advantages of this invention will become apparent from the following description taken in conjunction with any accompanying drawings wherein are set forth, by way of illustration and example, certain embodiments of this invention. Any drawings contained herein constitute a part of this specification and include

DETAILED DESCRIPTION OF THE INVENTION

Figure 1:
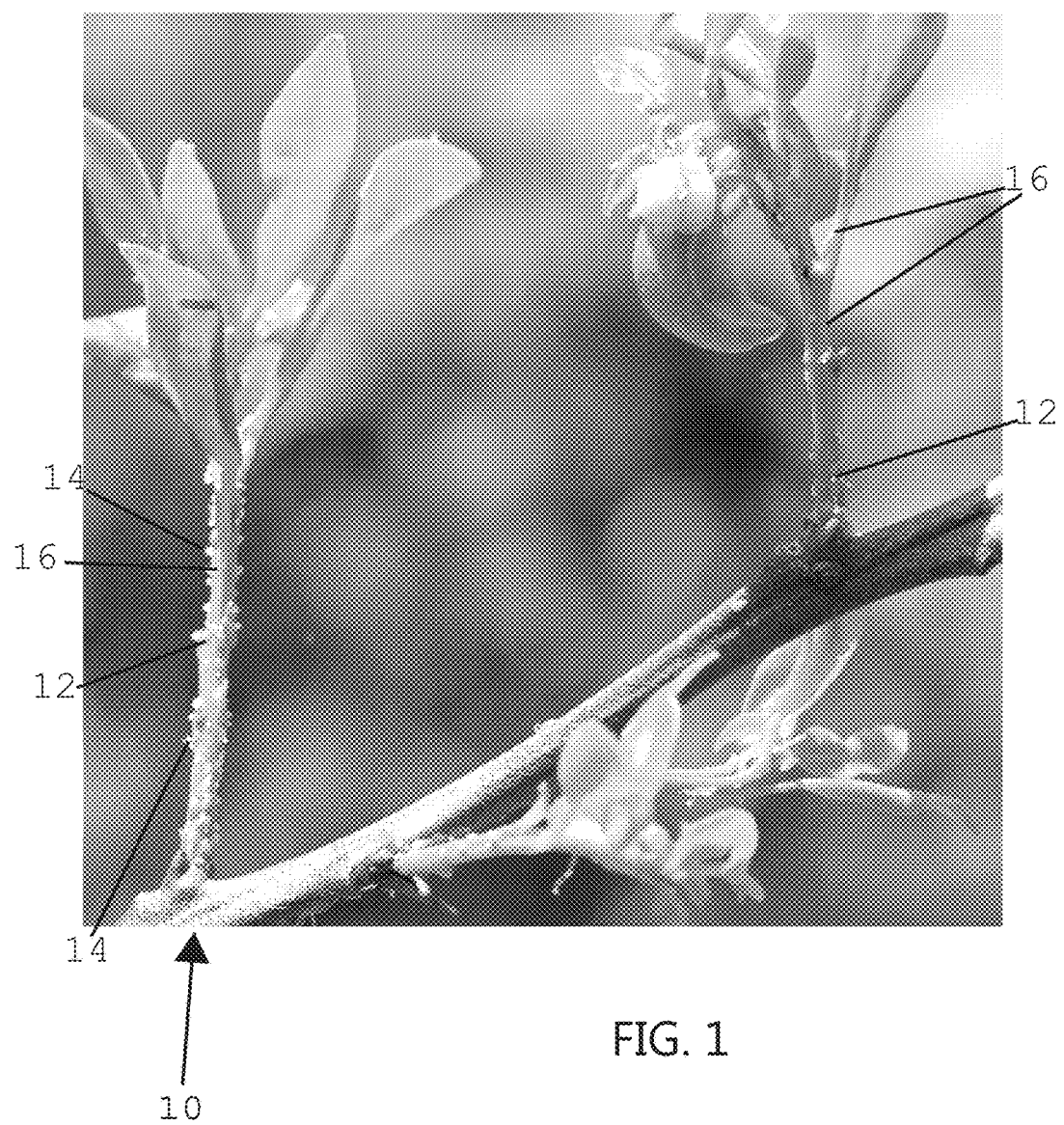
FIG. 1 illustrates a HLB positive citrus plant, illustrating the leaf and petioles infected with citrus psyllid.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

The present invention provides a composition, and use of the composition, for the treatment of plants inflicted with a bacterial disease. The plants, preferably flowering plants, and more preferable citrus plants, are inflicted with a bacterial disease transmitted by a psyllid vector, such as the Asian citrus psyllid, which causes Huanglongbing (HLB), or citrus greening disease. While these are the preferred and/or illustrative embodiments, the vectors, bacterium, plants, and plant diseases described herein are illustrative and not meant to be limiting. The composition of the present invention uses two antimicrobial components that are combined in a novel fashion to form a new chemical molecule with photocatalytic action, surface binding, and antimicrobial properties. The composition comprises 1) an organosilane, preferably an organosilane quaternary ammonium, and 2) a photocatalyst, such as titanium dioxide (TiO2). The composition is believed to be effective by utilizing one or more characteristics. The organosilane imparts positive charge on the composition. The positive charge attracts the negatively charged microbe. The organosilane component is further believed to puncture and chemically kill the microbe. Finally, the titanium dioxide (TiO2) is believed to reduce pathogens through the reactive oxidative stress (ROS) process.

In general, organosilane chemistry involves monomeric silicon chemicals known as silanes. A silane that contains at least one carbon-silicon bond (Si—C) structure is known as an organosilane. The organosilane molecule (Formula 1) has three key elements:

X—R—Si(OR')3            (Formula 1)

Wherein: X is a non-hydrolyzable organic moiety. This moiety can be reactive toward another chemical (e.g., amino, epoxy, vinyl, methacrylate, sulfur) or nonreactive (e.g., alkyl; wherein OR' is a hydrolyzable group, like an alkoxy group (e.g., methoxy, ethoxy isopropoxy) or an acetoxy group that can react with various forms of hydroxyl groups present in mineral fillers or polymers and liberates alcohols (methanol, ethanol, propanol) or acid (acetic acid). These groups can provide the linkage with inorganic or organic substrate; and wherein R is a spacer, which can be either an aryl or alkyl chain, typically propyl-. [R'=Methyl, Ethyl, Isopropy, R=Aryl or Alkyl (CH2)n with n=0, 1 or 3].

Typical organosilane quaternary compounds in accordance with the present invention include, but are not limited to: 3-(trimethoxysilyl)propyldimethyloctadecyl ammonium chloride; 3-(trimethoxysilyl)propyldidecylmethyl ammonium chloride; 3-(trimethoxysilyl)propyltetradecyldimethyl ammonium chloride; 3-(trimethoxysilyl)propyldimethylsoya ammonium chloride; 3-(trimethoxysilyl)propyldimethyloleyl ammonium chloride; 3-(trimethoxysilyl)propyloctadecyl ammonium chloride; 3-(trimethoxysilyl)propyloleyl ammonium chloride; 3-(trihydroxysilyl)propyldimethyloctadecyl ammonium chloride; 3-(trimethoxysilyl)propyldocosane ammonium chloride, 3-(trimethoxysilyl)propylmethyldi(decyl) ammonium chloride; 3-chhlorpropyltrimethoxysilane; octadecyltrimethoxysaline; perfluorooctyltriethoxysaline; benzalkonium chloride; or glycine betaine, or siltrane compounds (alkanoalmine in combination with organosilicon quaternary ammonium) as described in U.S. Pat. No. 5,064,613.

Preferably, titanium dioxide (TiO$_2$) is used as in the nano particle form. Accordingly, reference to TiO$_2$ includes titanium dioxide nanoparticles, including TiO$_2$, anatase grade. TiO$_2$ can be doped with other elements to make it more responsive to a wider range of light, including but not limited to zinc oxide, zirconium dioxide, nitrogen, silicone, silver (Ag), Carbon, Iron, or Copper.

As such, the composition is both an organosilane surface binding molecule and a photocatalytic molecule. The composition forms a multi-functional, anti-microbial biocide having several of the following characteristics: 1) a silane base which serves to combine the molecules together and to other surfaces, such as silica of plant surfaces; 2) the molecule contains a positively charged component for attracting microbes towards the molecule; 3) a long chain (i.e. chain of 5 or more carbons, such as for example, carbon chain having at least 17 $CH_2$ groups) for mechanically and chemically puncturing, as well as chemically neutralizing microbes; and 4) a photocatalytically activating molecule, creating a reactive oxygen and hydroxyl radical environment which oxidizes microbes.

TABLE 1

Example 1. Composition for treating plants infected with HLB.

| Component | Concentration |
| --- | --- |
| Organosilane | The concentrated composition is composed of 1 part Organosilane to 2 parts light activated photocatalyst |
| Photocatalyst | |
| Water | QS w/concentrated composition to desired effective concentration |

TABLE 2

Example 2. Composition for treating plants infected with HLB.

| Component | Concentration |
| --- | --- |
| Quaternary ammonium | The concentrated composition is composed of 1 part quaternary compound to 2 parts light activated photocatalytic agent |
| Light activated photocatalytic agent | |
| Water | QS w/concentrated composition to desired effective concentration |

TABLE 3

Example 3. Composition for treating plants infected with HLB.

| Component | Concentration |
| --- | --- |
| Organosilane quaternary ammonium | Concentrated composition is composed of 1 part organosilane quaternary ammonium to 2 parts $TiO_2$ |
| Titanium dioxide | |
| Water | QS w/ concentrated composition to desired effective concentration |

TABLE 4

Example 4. Composition for treating plants infected with HLB.

| Component | Concentration |
| --- | --- |
| 3-(Trihydroxysilyl)propyldimethyl-octadecyl ammonium chloride | Concentrated composition is composed of 1 part 3-(Trihydroxysilyl)propyldimethyl-octadecyl ammonium chloride to 2 parts Sol Gel Titanium Dioxide |
| Sol Gel Titanium Dioxide | |
| Water | QS w/ concentrated composition to desired effective concentration |

Preferably, the composition is composed of 2 parts $TiO_2$ to 1 part organosilane quaternary compound to form a concentrated compound. The concentrated compound is diluted approximately 20:1 for an applied concentration dosage of approximately 1000-1250 ppm.

Figure 2:
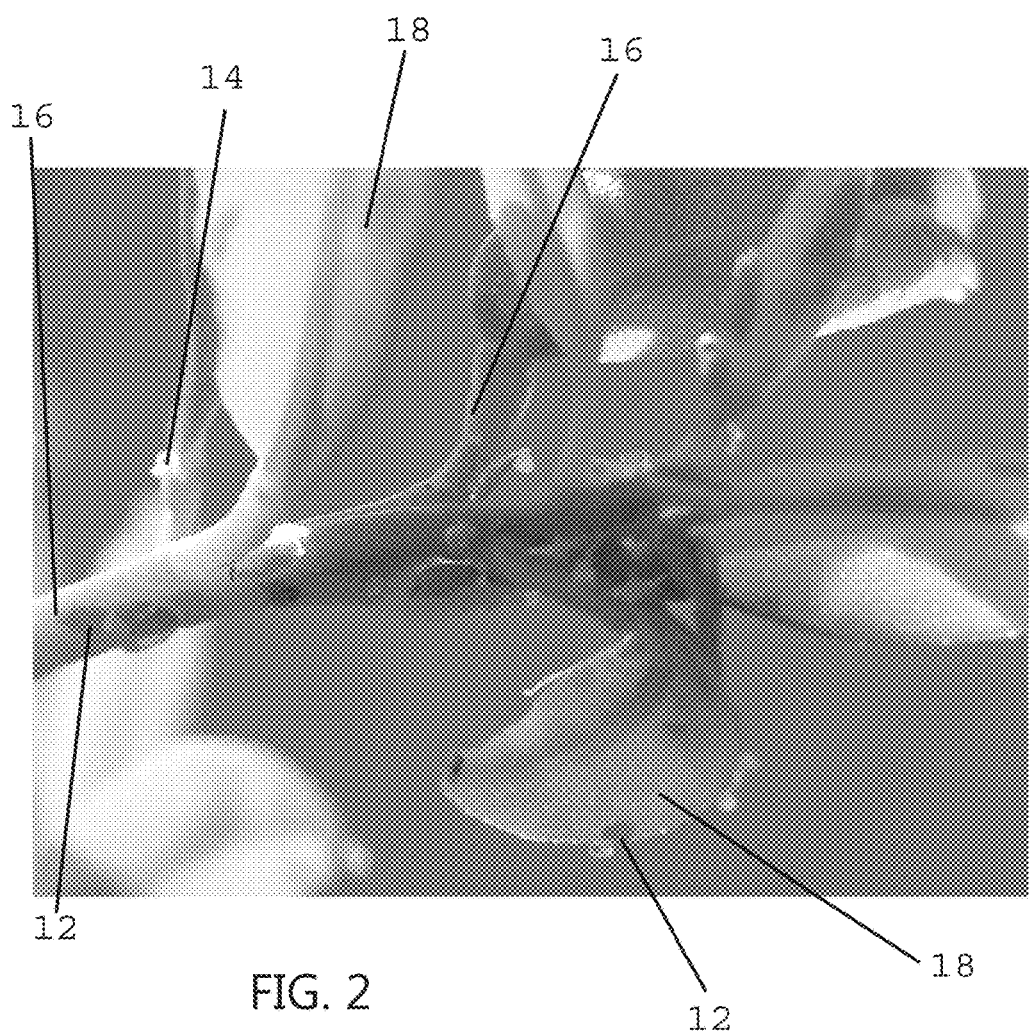
FIG. 2 is a close up view of a HLB positive citrus plant, illustrating psyllid and waxing of the petiole and lamina.

Initial Experiments: The composition described in Example 4 was applied to a variety of citrus trees growing in residential areas. All citrus trees were identified as HLB (CLas)-positive prior to application of the composition. Prior to the start of the study, candidate trees were observed as having multiple sites of psyllid infection, with waxing and larvae identification. Referring to FIGS. 1 and 2, candidate citrus trees 10 are shown with psyllid 12 and psyllid wax 14 infestations located on the plant or leaf petiole 16 and/or lamina 18. In addition, all trees had some form of mottling or yellow leaves (not shown). Trees inflicted with HLB were identified using a rapid screening process, DNABLE assay method for detecting DNA for *Liberibacter asiaticus* (CLas) in leaf petioles, developed by Envirologix (Portland, Me., USA).

The DNAable assay detection test was designed as an isothermal nucleic acid amplification technology enabling rapid amplification of specific DNA targets. Samples were processed and assayed according to manufacture protocols and directions. Briefly, leaf and petiole samples were obtained from citrus trees suspected of infection with HLB. Samples were refrigerated or frozen if not used immediately. Pieces of petiole were collected and added to iced, MB5 Extraction Buffer. The sample was heated at 95 degrees Celsius for 5 minutes. A second buffer was then added to the sample, and mixed. Sample assaying followed.

Figure 4:
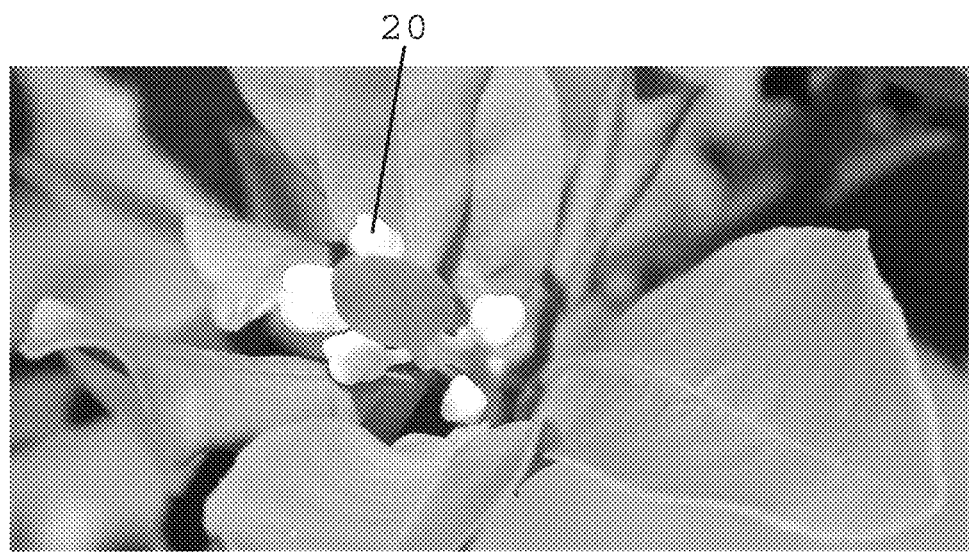
FIG. 4 illustrates a citrus plant seven to ten days after initial treatment with the composition, illustrating initial blooming.
Figure 5:
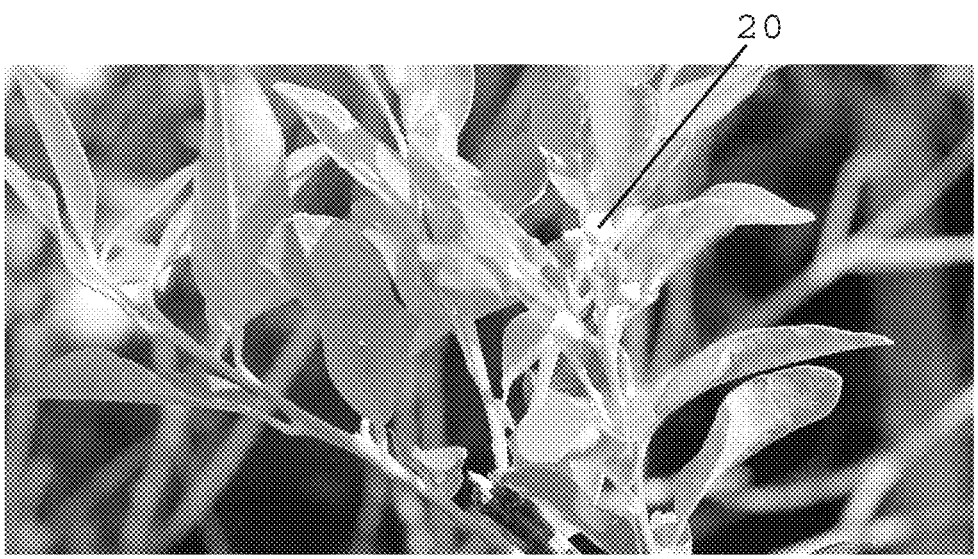
FIG. 5 illustrates the citrus plant seven to ten days after initial treatment with the composition, illustrating initial blooming.

Each positively identified HLB tree was administered the composition via a foliar spray and a root drench every 7 days. After each 7 day treatment, DNAable assay was performed on the leaf samples to verify the presence or absence of HLB. Within 2-3 days, a systemic effect was observed, and the killing of psyllid, larva and eggs was observed, see FIG. 3. Within 7-10 days after the initial treatment, several citrus trees had undergone a bloom 20, see FIGS. 4 and 5.

Figure 3:
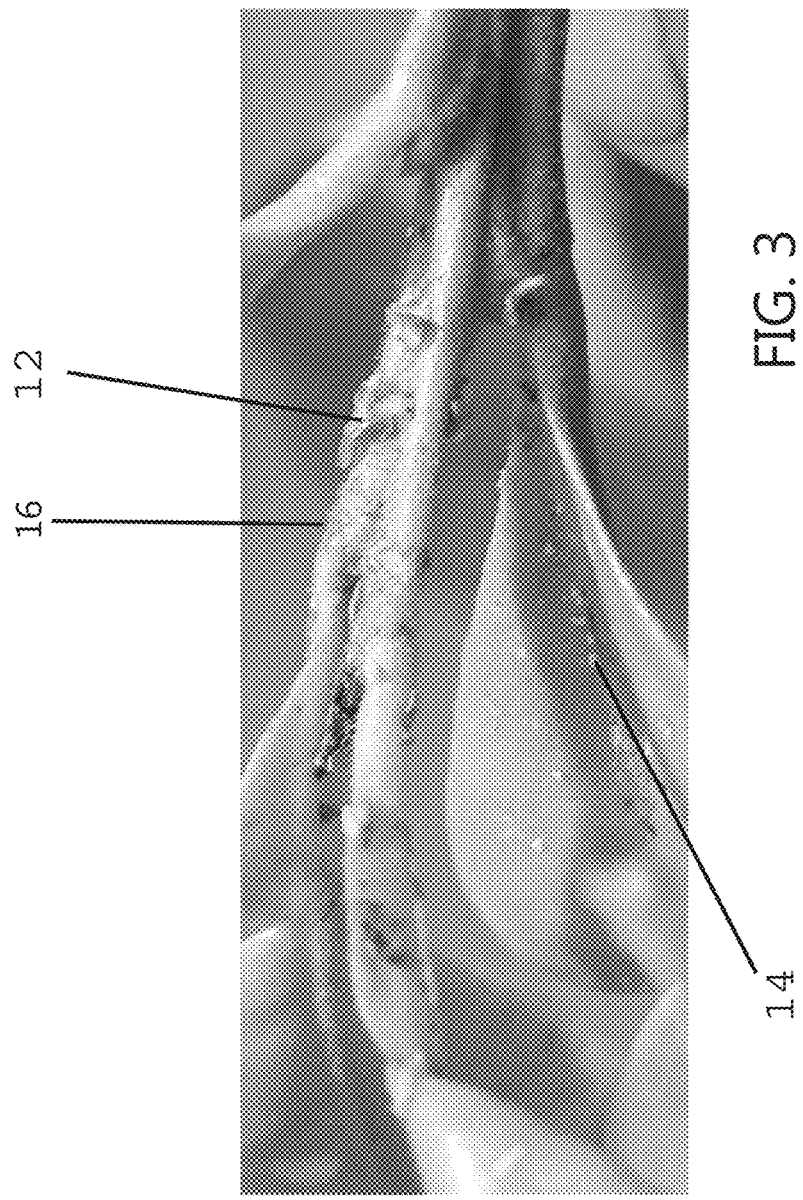
FIG. 3 illustrates a citrus plant three days after initial treatment with the composition.
Figure 6:
FIG. 6 illustrates a representative citrus tree prior to treatment with the composition.
Figure 7:
FIG. 7 illustrates a representative citrus tree two to three weeks post treatment with the composition.
Figure 8:
FIG. 8 illustrates a representative citrus tree six weeks post treatment with the composition.
Figure 9:
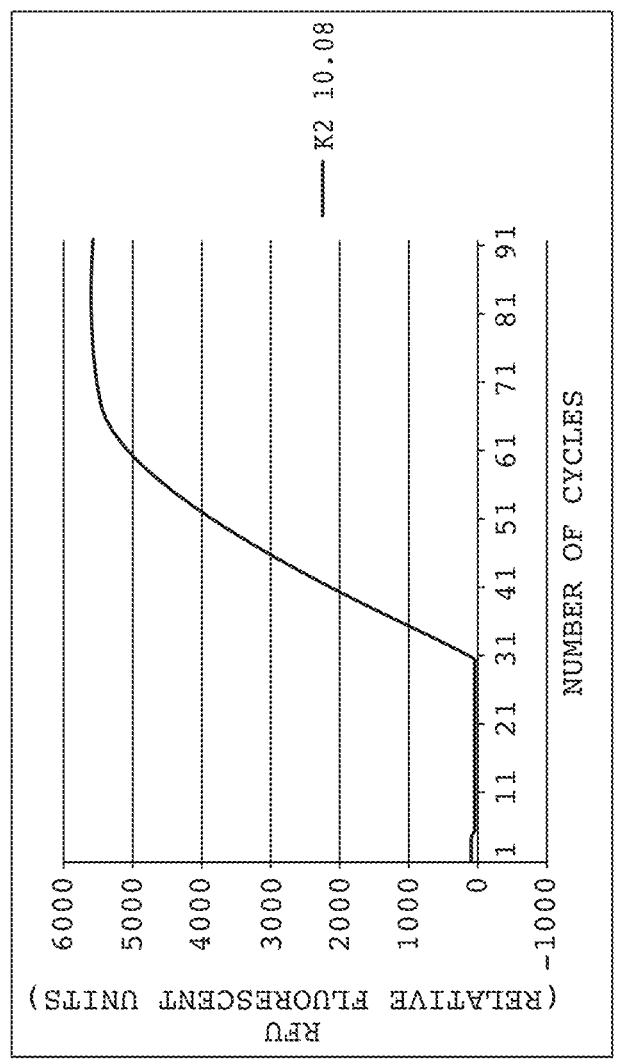
FIG. 9 is a graph illustrating the results of the DNABLE assay administered to plants prior to treatment with the composition, indicating a positive indication for HLB in the tested plants.
Figure 10:
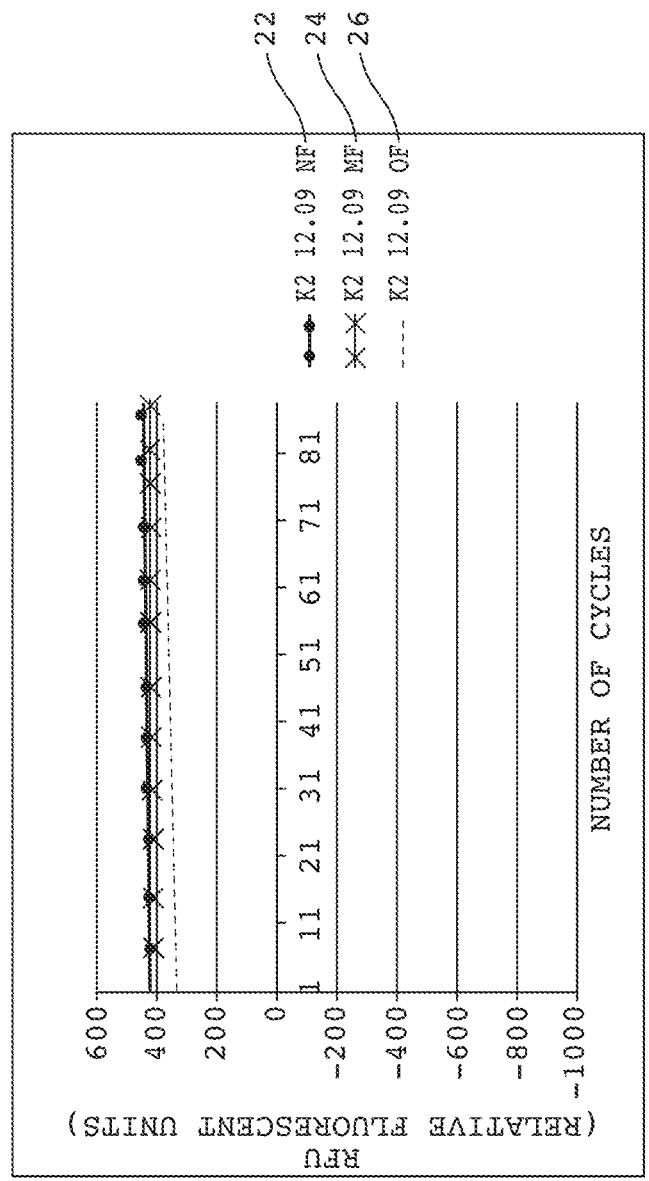
FIG. 10 is a graph illustrating the results of the DNABLE assay after treatment with the composition, indicating a negative indication for HLB in samples taken from new, medium, and old leaves of the citrus tree.
Figure 11:
FIG. 11 illustrates infected trees about three months after treatment with the composition, assays indicated that the plants were HLB negative, the healthy plant having new flush.
Figure 12:
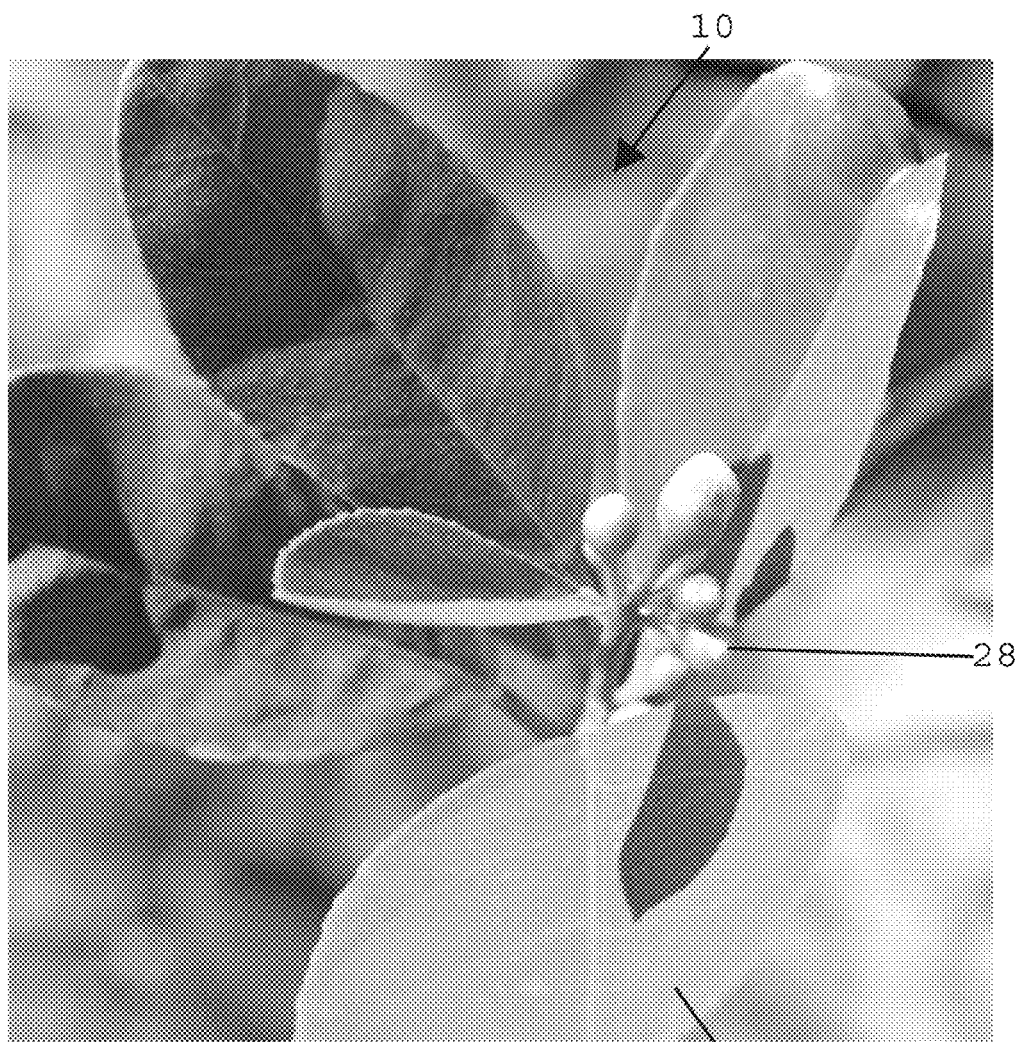
FIG. 12 illustrates infected trees about three months after treatment with the composition, assays indicated that the plants were determined to be HLB negative, the healthy plant is shown having new budding.
Figure 13:
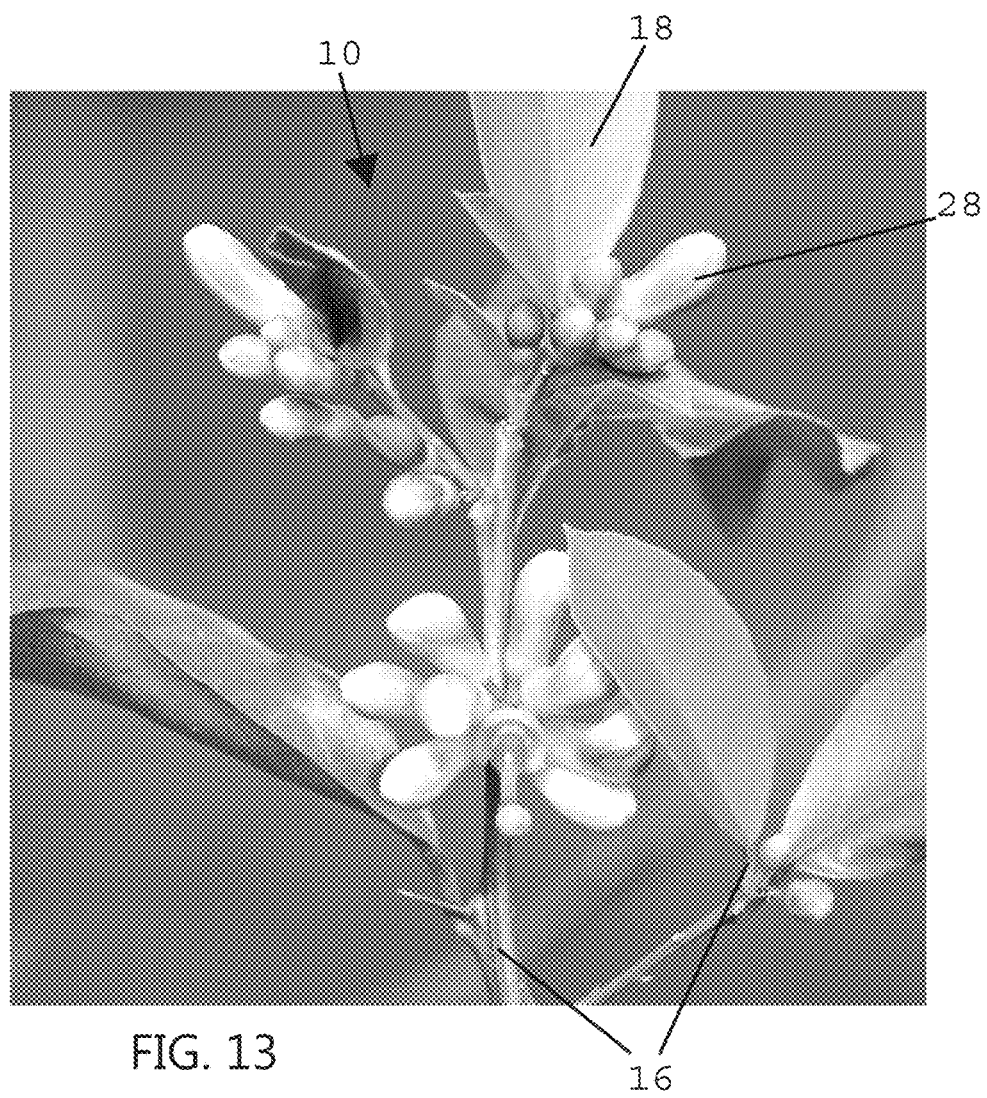
FIG. 13 illustrates infected trees about three months after treatment with the composition; assays indicated the plants were HLB negative, the healthy plant is shown having improved overall health.

Two to three weeks post initial treatment, several of the trees underwent massive leaf drop. After 6 weeks, the trees observed having leaf drop tested negative for HLB, (see FIGS. 6-8: FIG. 6, pre-treatment; FIG. 7, 2-3 weeks post initial treatment; and FIG. 8, 6 weeks post initial treatment). Within 3 months, all treated trees were negative for the HLB. FIG. 9 illustrates test results from those infected trees testing positive for HLB prior to treatment. FIG. 10 illustrates test results from new leaves, 22, medium leaves 24, and old leaves 26 obtained from treated trees and tested using the DNABLE assay method. The results indicate that the samples obtained were negative for HLB. In addition to the DNABLE assay, the trees were observed to have significant amounts of new flush, budding (see ref. indicator 28), and improved visual appearance of health, see FIGS. 11-13.

Figure 14:
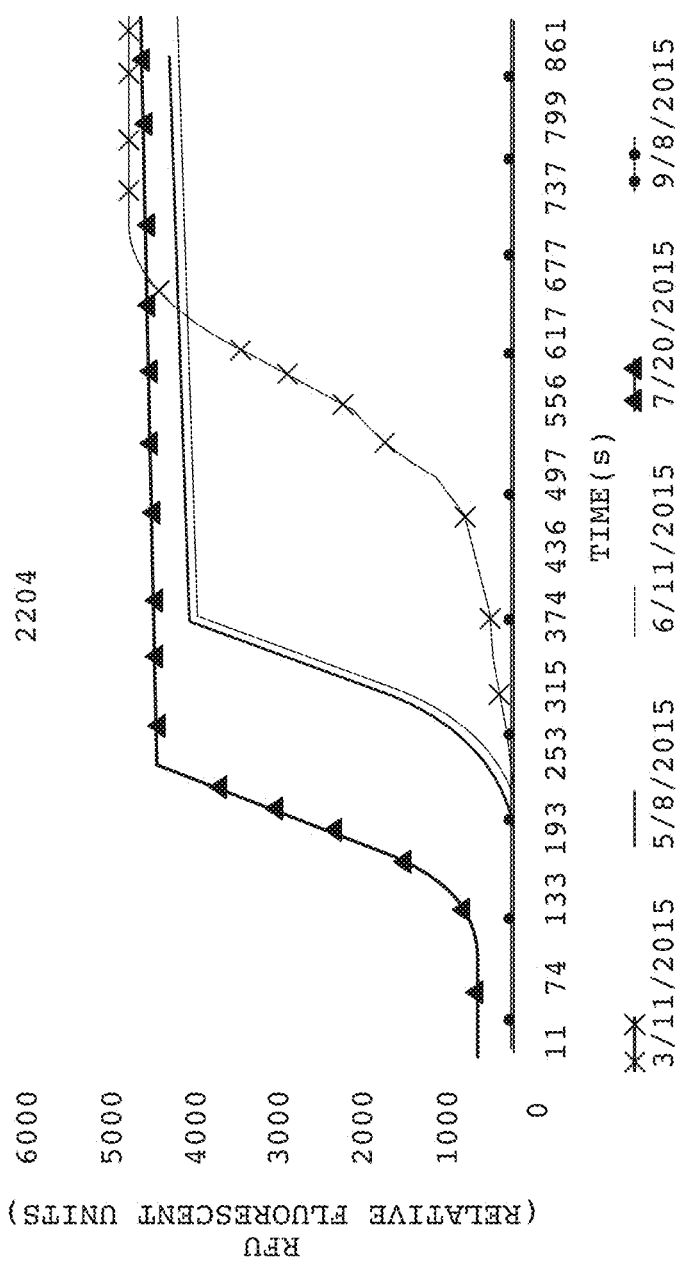
FIG. 14 is a graph illustrating the results of testing for the presence of HLB in Tree 2204 prior to and after six months of treatment with the composition.
Figure 15:
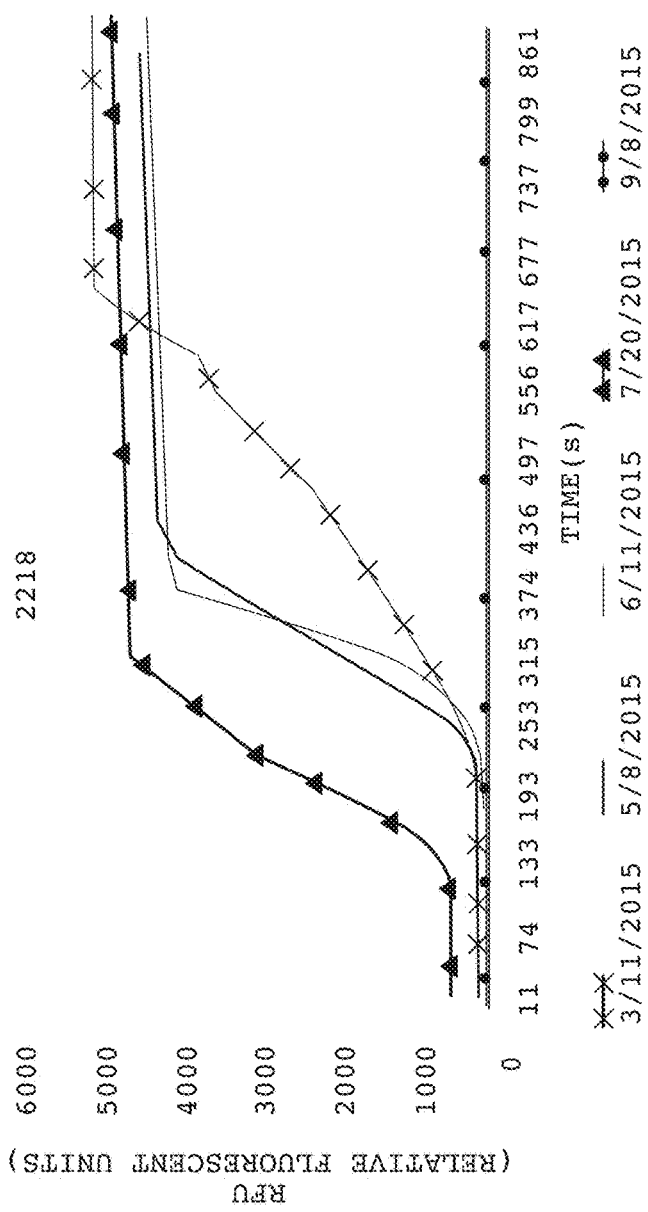
FIG. 15 is a graph illustrating the results of testing for the presence of HLB in Tree 2218 prior to and after six months of treatment with the composition.
Figure 16:
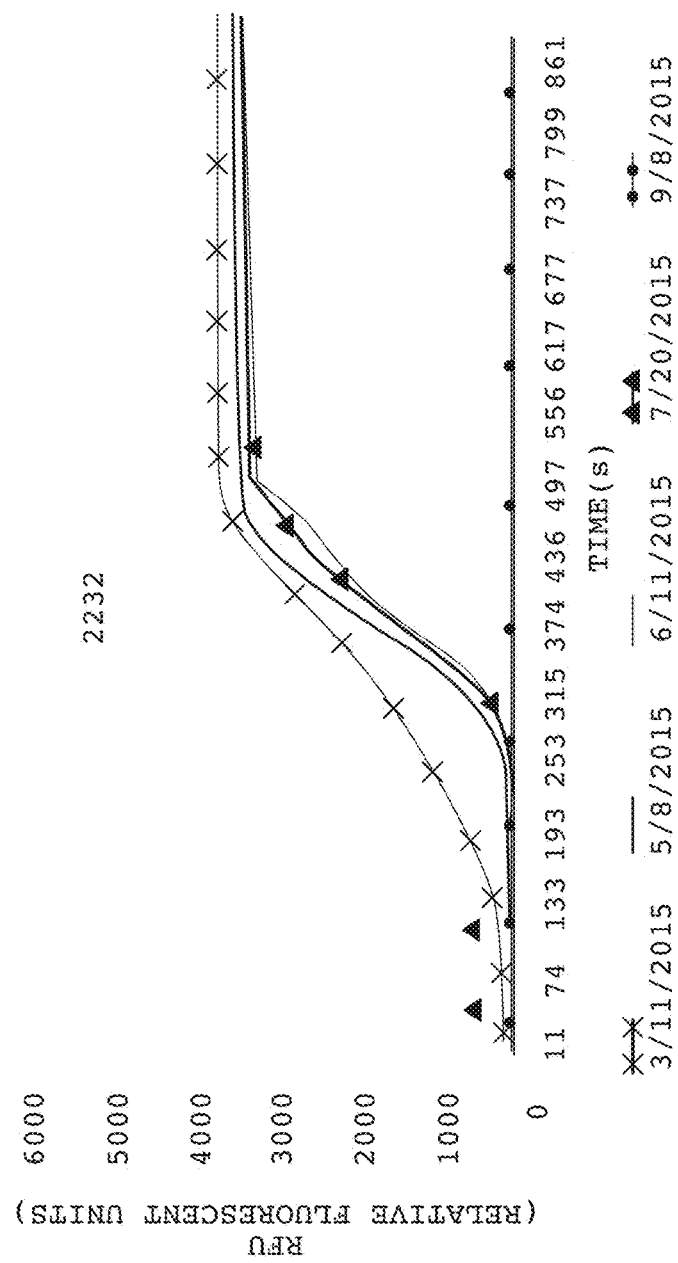
FIG. 16 is a graph illustrating the results of testing for the presence of HLB in Tree 2232 prior to and after six months of treatment with the composition.

Additional Testing: Phase 2. Additional HLB positive trees (identified using DNABLE assay) from an independent crop were identified and treated. The initial testing sample size was 35 trees. Samples were taken prior to treatment, as well as additional intervals up to at least 6 months. The canopy and root systems of the test subject trees were treated with two gallons of treatment solution in accordance with the present invention every two weeks. For trees showing excessive leaf drop and tree stress, treatment delivery was temporarily suspended until the trees showed signs of recovery. Two gallon, bi-weekly root drench was continued for at least another 3 months. Of the original 35 test trees, 19 were determined to be HLB(+). During the testing period, samples were taking at various time periods to determine the status of the tree. Approximately 42% (8 trees) of the trees that were HLB(+) prior to treatment were found to be HLB(−) after treatment. FIGS. 14-16 are graphs of representative HLB(+) trees treated with the composition in accordance with the invention and found to be HLB(−) over a 6 month treatment time. FIG. 14 illustrates the data for Tree 2204. FIG. 15 illustrates the data for Tree 2218. FIG. 16 illustrates the data for Tree 2232. In each of the graphs, the Y-axis corresponds to how well test samples measure to a light active DNA sensitive material specifically designed to detect CLasHLB bacteria. Values over 1,000 are deemed a positive test result for the presence of the bacteria. The X-axis illustrates the reaction over time (seconds). As shown in FIG. 14, Tree 2204 was initially infected with the HLB bacteria. By the end of the treatment, the tree was determined to be HLB negative. Such data illustrates the ability of the Applicant's composition to change a positively identified tree to a negative tree. Tree 2218 (FIG. 15) and Tree 2232 (FIG. 16) illustrate similar results.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for treating or protecting a citrus plant comprising:
    applying, via a foliar spray or root drench, a composition to one or more components of a viable citrus plant or citrus plant part inflicted with, exposed to, or predisposed to Huanglongbing (HLB), or citrus greening disease, which upon application is transported into said plant vasculature;
    said composition free of alcohol and configured for absorption into said plant's vasculature system via stomata sites or via root drenching to attack specific plant pathogens associated with Huanglongbing (HLB), or citrus greening disease, said composition comprising:
    an organosilane having a saline base and a positively charged component;
    a photocatalytically activated molecule;
    said organosilane and said photocatalytically activated molecule in sufficient concentration, which, in combination, is sufficient to treat said viable citrus plant or citrus plant part inflicted with, exposed to, or predisposed to said Huanglongbing (HLB), or citrus greening disease.

2. The method for treating or protecting a citrus plant according to claim 1 wherein said disease is a result of a vasculature system limiting bacterial pathogen.

3. The method for treating or protecting a citrus plant according to claim 1 wherein said pathogen is a vasculature system limiting bacterial pathogen.

4. The method according to claim 1 wherein said photocatalytically activated molecule is a metal-oxide crystalline mineral catalyst.

5. The method according to claim 1 wherein said photocatalytically activated molecule is a nano particle metal-oxide crystalline mineral catalyst.

6. The method according to claim 1 wherein said organosilane is an organosilane quaternary compound.

7. The method according to claim 6 wherein said organosilane quaternary compounds are:
    3-(trimethoxysilyl)propyldimethyloctadecyl ammonium chloride;
    3-(trimethoxysilyl)propyldidecylmethyl ammonium chloride;
    3-(trimethoxysilyl)propyltetradecyidimethyl ammonium chloride;
    3-(trimethoxysilyl)propyldimethylsoya ammonium chloride;
    3-(trimethoxysilyl)propyldimethyloleyl ammonium chloride;
    3-(trimethoxysilyl)propyloctadecyl ammonium chloride;
    3-(trimethoxysilyl)propyloleyl ammonium chloride;
    3-(trihydroxysilyl)propyldimethyloctadecyl ammonium chloride;
    3-(trimethoxysilyl)propyldocosane ammonium chloride;
    3-(trimethoxysilyl)propylmethyldi(decyl) ammonium chloride;
    3-chhlorpropyltrimethoxysilane; octadecyltrimethoxysaline;
    perfluorooctyltriethoxysaline; benzalkonium chloride; or glycine betaine, or siltrane compounds.

8. The method according to claim 1 wherein said photocatalytically activated molecule is titanium dioxide.

9. The method according to claim 8 wherein said titanium dioxide is used as a nano particle form.

10. The method according to claim 8 wherein said titanium dioxide is $TiO_2$ anatase grade.

11. The method according to claim 8 wherein said titanium dioxide is doped with an additional agent.

12. The method according to claim 11 wherein said titanium dioxide is doped with zinc oxide, zirconium dioxide, nitrogen, silicone, silver, carbon, iron, or copper.

\* \* \* \* \*